(12) United States Patent  
Harding

(10) Patent No.: US 7,904,170 B2
(45) Date of Patent: *Mar. 8, 2011

(54) RADIO FREQUENCY TRANSPONDER BASED IMPLANTABLE MEDICAL SYSTEM

(75) Inventor: William C. Harding, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/845,445

(22) Filed: Jul. 28, 2010

(65) Prior Publication Data

US 2010/0312309 A1 Dec. 9, 2010

Related U.S. Application Data

(63) Continuation of application No. 12/019,683, filed on Jan. 25, 2008, now Pat. No. 7,792,588.

(60) Provisional application No. 60/886,837, filed on Jan. 26, 2007.

(51) Int. Cl.
*A61N 1/00* (2006.01)

(52) U.S. Cl. .......................................... 607/60

(58) Field of Classification Search ...................... 607/60
See application file for complete search history.

(56) References Cited

U.S. PATENT DOCUMENTS

| 5,109,845 A | 5/1992 | Yuuchi et al. |
| 5,324,316 A | 6/1994 | Schulman et al. |
| 5,411,535 A | 5/1995 | Fugi et al. |
| 5,814,089 A | 9/1998 | Stokes et al. |
| 5,954,758 A | 9/1999 | Peckham et al. |
| 6,141,588 A | 10/2000 | Cox et al. |
| 6,488,704 B1 | 12/2002 | Connelly |
| 7,114,502 B2 | 10/2006 | Schulman et al. |
| 2004/0147973 A1 | 7/2004 | Hauser |
| 2006/0224206 A1 | 10/2006 | Dublin et al. |
| 2007/0088394 A1 | 4/2007 | Jacobson |
| 2007/0233204 A1 | 10/2007 | Lima et al. |

FOREIGN PATENT DOCUMENTS

| NL | 9301064 | 1/1995 |
| WO | WO 00/16686 | 3/2000 |
| WO | WO 2006/065394 | 6/2006 |
| WO | WO 2008/034005 | 3/2008 |

OTHER PUBLICATIONS

International Search Report for PCT application No. PCT/US2009/031387, Aug. 3, 2009; 5 pgs.

*Primary Examiner* — Niketa I Patel
*Assistant Examiner* — Shubatra Narayanaswamy
(74) *Attorney, Agent, or Firm* — Michael J. Ostrom; Stephen W. Bauer

(57) ABSTRACT

An implantable medical device (IMD) system includes an IMD, a transceiver antenna lead for the IMD, and a wireless therapy delivery transponder or probe that is remotely activated by the IMD via the transceiver antenna lead. The IMD and the wireless probe communicate using wireless RF-based transponder techniques. The wireless probe includes a capacitor that is charged when the IMD emits an appropriate electromagnetic field from the transceiver antenna lead. The wireless probe delivers electrical therapy in the form of electrical pulses from the capacitor in response to RF activation signals emitted by the IMD via the transceiver antenna lead.

25 Claims, 11 Drawing Sheets

RADIO FREQUENCY TRANSPONDER BASED IMPLANTABLE MEDICAL SYSTEM

This is a continuation of application Ser. No. 12/019,683, filed Jan. 25, 2008, (allowed), which is incorporated herein by reference and which claims the benefit of U.S. provisional application No. 60/886,837, filed Jan. 26, 2007.

TECHNICAL FIELD

The present invention relates generally to implantable medical devices (IMD), and, more particularly, to the use of radio frequency (RF) transponder technology with an IMD that delivers electrical therapy from a wireless RF transponder/probe to body tissue or fluid.

BACKGROUND

IMDs provide therapies to patients suffering from a variety of conditions. IMDs can be utilized in a variety of applications, such as drug or fluid delivery, monitors, and therapeutic devices for other areas of medicine, including metabolism, endocrinology, hematology, neurology, muscular disorders, gastroenterology, urology, ophthalmology, otolaryngology, orthopedics, and similar medical subspecialties. Many IMDs are designed to generate and deliver electrical pulses to stimulate body tissue, muscles, body fluid, etc.

Examples of IMDs involving cardiac devices are implantable pacemakers and implantable cardioverter-defibrillators (ICDs). Such cardiac IMDs typically monitor the electrical activity of the heart and may provide electrical stimulation to one or more of the heart chambers when necessary. For example, pacemakers are designed to sense arrhythmias, i.e., disturbances in heart rhythm, and, in turn, provide appropriate electrical stimulation pulses at a controlled rate to selected chambers of the heart in order to correct the arrhythmias and restore the proper heart rhythm.

ICDs also detect arrhythmias and provide appropriate electrical stimulation pulses to selected chambers of the heart to correct the abnormal heart rate. In contrast to pacemakers, however, an ICD can also provide pulses that are much stronger and less frequent, where such pulses are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy therapy pulses to the heart.

FIG. 1 is an illustration of a prior art IMD 100 implanted in the body of a patient 102. FIG. 1 also depicts an external communication device (such as a programmer 104) that is not implanted within patient 102. Telemetry communications can take place between IMD 100 and programmer 104 using known wireless telemetry techniques and technologies. The arrows in FIG. 1 represent such telemetry communications. In practice, a given communication session between programmer 104 and IMD 100 may be unidirectional or, as illustrated, bidirectional.

Programmer 104 permits non-invasive communication with IMD 100, where such communication is enabled via downlink and uplink communication channels. Generally, any form of portable programmer, interrogator, recorder, monitor, or telemetered signals transmitter and/or receiver found suitable for communicating with IMD 100 could be used for programmer 104. Programming commands or patient data can be transmitted between one or more antennas of IMD 100 and one or more antennas of programmer 104.

When IMD 100 is used for cardiac applications (e.g., to provide cardiac sensing, pacing, and/or defibrillation functions for patient 102), IMD 100 can be a cardiac device—for example, a pacemaker, an ICD, a hemodynamic monitor, or the like. IMD 100 is implanted beneath the skin or muscle of patient 102. When IMD 100 is used for cardiac applications (as shown in FIG. 1), IMD 100 is electrically coupled to the heart 106 of the patient 102 through electrodes connected to one or more leads 108. The leads 108 are routed inside the heart 106 such that the electrodes can be attached within the heart 106 at the desired location. The leads 108 are typically coupled to a connector block 110 of IMD 100 in a manner well known in the art.

Various desirable features and characteristics will become apparent from the subsequent detailed description and the appended claims, taken in conjunction with the accompanying drawings and the foregoing technical field and background.

BRIEF SUMMARY

An IMD system as described herein is suitably configured to deliver electrical therapy and/or to receive physiologic sensor data via RF transponder(s) in lieu of endocardial leads that are physically connected to the IMD. The IMD system utilizes RF transponder technology to induce energy into a wireless semi-passive RF probe, and to control the use of the induced energy for the desired purpose, such as cardiac sensing, pacing, and/or defibrillation, muscle stimulation, or the like. An existing IMD platform may be modified to support the RF transponder technology while preserving its core diagnostic and therapy delivery functionality, and patient use of the IMD system need not differ from existing control and monitor protocols. The use of wireless RF probes in an ICD application eliminates the need to place leads in the heart or elsewhere. Consequently, this will enable a quicker implant and would eliminate potential difficulties in lead placement and removal.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
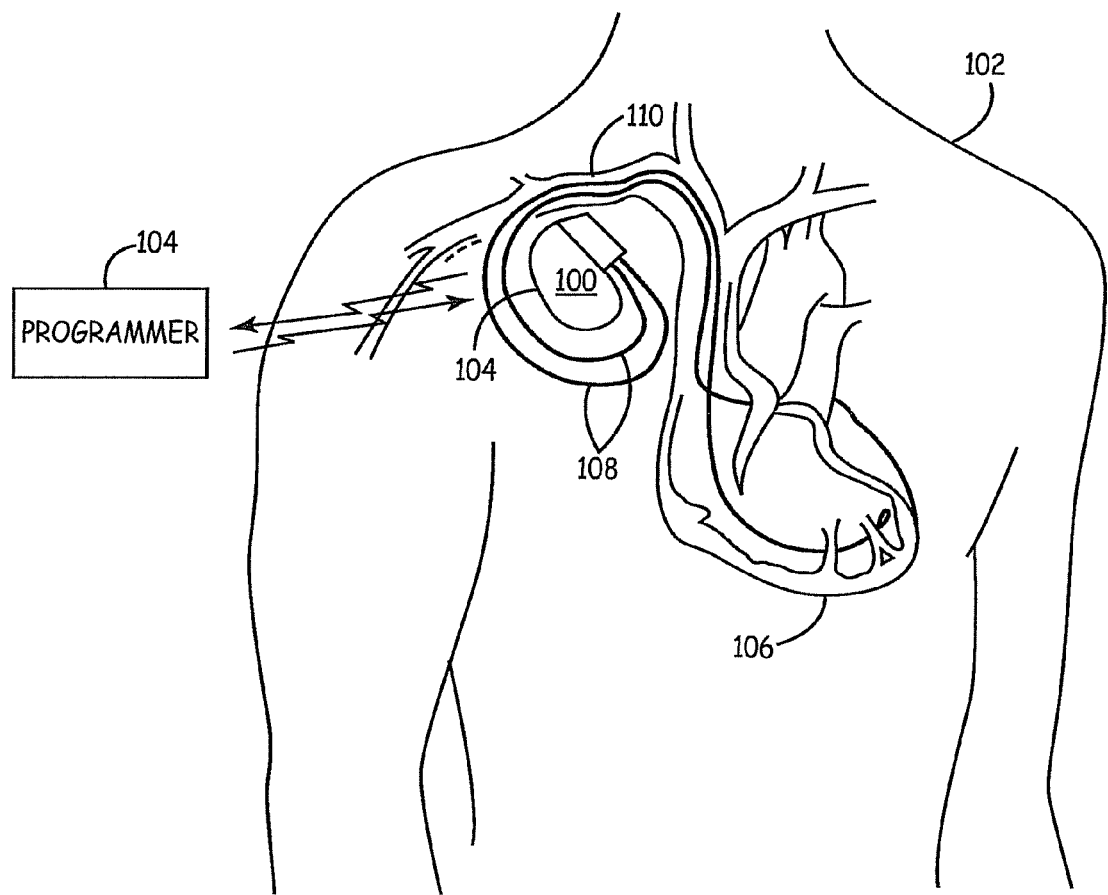
FIG. 1 is an illustration of an IMD in the body of a patient.

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

Subject matter may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present invention may be practiced in conjunction with any number of IMD configurations and applications, and that the system described herein is merely one example embodiment of the invention.

For the sake of brevity, conventional techniques and features related to IMDs, RF transponders, digital control logic, IMD transceivers, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description may refer to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict example arrangements of elements, additional intervening elements, devices, features, or components may be present in an embodiment of the invention.

The embodiments described herein can be implemented in an IMD that is configured to deliver electrical pulses as stimulation or therapy to body tissue, fluid, muscle, bone, etc., and/or any IMD that is configured to receive sensor data that is indicative of physiological electromagnetic activity. In lieu of traditional leads and electrodes, the present IMD system utilizes RF-based techniques to deliver electrical therapy to a wireless RF transponder and/or to receive sensor signals that convey electromagnetic activity detected by a wireless RF transponder. At present, a wide variety of IMDs are commercially available or proposed for clinical implantation. Such IMDs include pacemakers as well as ICDs, drug delivery pumps, cardiomyostimulators, cardiac and other physiologic monitors, nerve and muscle stimulators, deep brain stimulators, cochlear implants, and artificial organs (e.g., artificial hearts). In addition, as the technology advances, it is contemplated that IMDs will become even more complex with respect to programmable operating modes, menus of operating parameters, and monitoring capabilities of increasing varieties of physiologic conditions and electrical signals. It is to be appreciated that embodiments of the subject matter described herein will be applicable in such emerging IMD technology as well.

Figure 2:
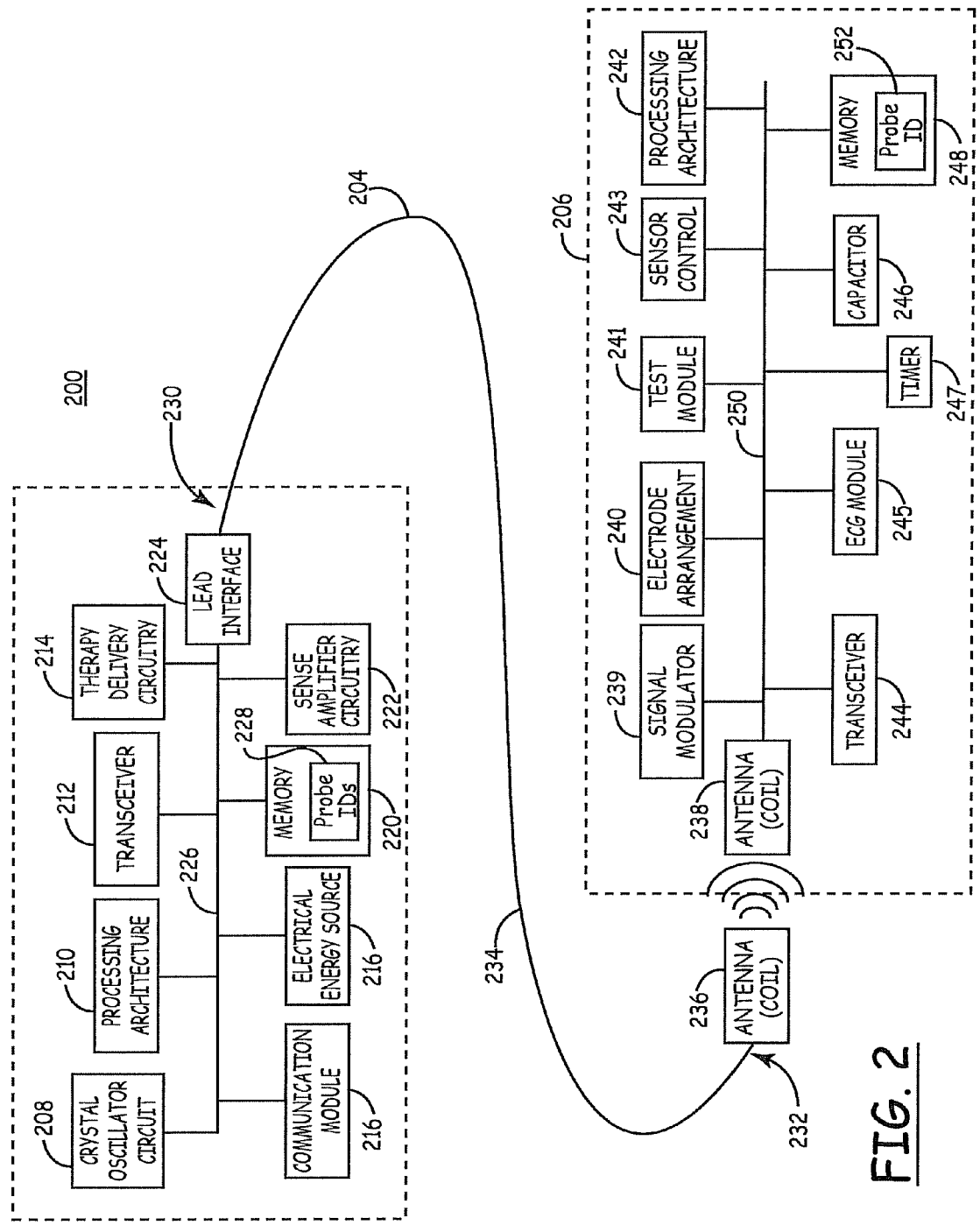
FIG. 2 is a schematic representation of an embodiment of an RF transponder based IMD system.

FIG. 2 is a schematic representation of an embodiment of an RF transponder based IMD system 200. System 200 generally includes, without limitation, an IMD 202, a transceiver antenna lead 204, and a wireless device 206. Wireless device 206 may be a semi-passive RF probe that is configured to operate as a wireless therapy delivery device for system 200. Depending upon the specific embodiment, wireless device 206 may also be configured to operate as a wireless sensor device that detects electromagnetic activity, which may be conducted by body tissue, body fluid, or the like. FIG. 2 depicts certain logical, functional, and operational modules and, components of IMD 202 and wireless device 206 in block diagram form for ease of description. In practice, all of the components of system 200 are intended to be implanted within the body of the patient.

IMD 202 may include hardware, software, firmware, and circuitry for managing the operation and function of IMD 202, with such features being contained within a hermetic enclosure of IMD 202. IMD 202 includes a number of electrical components, operating modules, and components such as, without limitation: a crystal oscillator circuit 208; a processing architecture 210; a transceiver 212; a therapy delivery circuit 214; a communication module 216; an electrical energy source 218; a suitable amount of memory 220, which may include random-access memory (RAM) and/or read-only memory (ROM); sense amplifier circuitry 222; and a lead interface circuit 224. These elements may be coupled together using, for example, a bus 226 or any suitably configured interconnection arrangement. Although not shown in FIG. 2, communication module 216 may cooperate with one or more antennas configured to enable IMD 202 to communicate with other devices (e.g., an external programmer). It should be appreciated that the configuration shown in FIG. 2 represents only one possible implementation of an IMD suitable for use with IMD system 200.

Although not a requirement, this example assumes that IMD system 200 is configured for cardiac applications (e.g., to provide cardiac sensing, pacing, and/or defibrillation functions for the patient). In certain embodiments, IMD 202 may include an implantable cardiac monitor without a therapy delivery function, e.g., an implantable ECG monitor for recording the cardiac electrogram from electrodes remote from the heart. Alternatively, IMD 202 may include an implantable hemodynamic monitor (IHM) for recording cardiac electrogram and other physiologic sensor derived signals, e.g., one or more of blood pressure, blood gases, temperature, electrical impedance of the heart and/or chest, and patient activity. In yet another embodiment, IMD 202 includes the combined functionality of sensing, pacing, and defibrillating.

Notably, in contrast to conventional cardiac IMD systems, endocardial electrode leads are not required in IMD system 200. Rather, IMD system 200 utilizes wireless device 206 (under the control of IMD 202) to deliver electrical therapy to the patient's heart as needed. In this regard, IMD 202 controls wireless device 206 via transceiver antenna lead 204. In this embodiment, the physical connection between transceiver antenna lead 204 and the various internal components of IMD 202 is facilitated by means of a suitably configured connector block assembly (shown in FIG. 3). Electrically, the coupling of the conductors of transceiver antenna lead 204 and internal electrical components of IMD 202 may be facilitated by means of lead interface circuit 224. In practice, lead interface circuit 224 may function, in a multiplexer-like manner, to selectively and dynamically establish necessary connections between various conductors in transceiver antenna lead 204 and individual electrical components of IMD 202, as would be familiar to those of ordinary skill in the art. For the sake of clarity, the specific connections between transceiver antenna lead 204 and the various components of IMD 202 are not shown in FIG. 2, although such connections will be familiar to those of ordinary skill in the art.

For cardiac applications, the conductors in transceiver antenna lead 204 may be coupled, either directly or indirectly, to sense amplifier circuitry 222 and to therapy delivery circuitry 214 to enable IMD system 200 to operate in the manner described in more detail herein. This configuration allows IMD 202 to transmit activation signals that convey operating commands to wireless device 206, via transceiver antenna lead 204. In addition, this configuration allows IMD 202 to transmit capacitor charge signals to wireless device 206, using transceiver 212 and transceiver antenna lead 204. Moreover, this configuration allows IMD 202 to receive signals from wireless device 206, via transceiver antenna lead 204.

As previously noted, IMD 202 includes processing architecture 210, which generally varies in sophistication and complexity depending upon the type and functional features of IMD 202. In practice, one or more of the modules or components of IMD 202 shown in FIG. 2 (or any portion thereof) may be realized in or executed by processing architecture 210, memory 220, and/or elsewhere in IMD 202. In certain embodiments, processing architecture 210 can be an off-the-shelf programmable microprocessor, a microcontroller, a custom integrated circuit, or any of a wide variety of other implementations generally known. Although specific connections between processing architecture 210 and other components of IMD 202 are not shown in FIG. 2, it will be apparent to those of ordinary skill in the art that processing architecture 210 functions to control the timed operation of sense amplifier circuitry 222 and therapy delivery circuitry 214. In certain embodiments, the functioning of processing architecture 210 would be under the control of firmware or programmed software algorithms stored in memory 220 (e.g., RAM, ROM, PROM and/or reprogrammable ROM), which are carried out using a processing unit of a typical microprocessor core architecture. In certain embodiments, processing architecture 210 can also include a watchdog circuit, a DMA controller, a lock mover/reader, a CRC calculator, and other specific logic circuitry coupled together by on-chip bus, address bus, and power, clock, and control signal lines in paths or trees in a manner well known in the art.

In certain embodiments, as is known in the art, electrical energy source 218 powers IMD 202 and can also be used to power electromechanical devices, such as valves or pumps, of a substance delivery IMD. Moreover (although not required considering the use of wireless device 206 for the delivery of electrical therapy), electrical energy source 218 may also be utilized to provide electrical stimulation energy of an ICD pulse generator, cardiac pacing pulse (IPG) generator, or other electrical stimulation and sensing generator in accordance with legacy systems. In one preferred embodiment, IMD 202 is suitably configured to recharge electrical energy source 218 by electromagnetic coupling with an external apparatus using inductive and propagation coupling techniques. In practice, electrical energy source 218 may be coupled to a power supply circuit having power-on-reset (POR) capability. The power supply circuit can provide one or more low voltage power supply signals, the POR signal, one or more voltage reference sources, current sources, an elective replacement indicator (ERI) signal, etc. For the sake of clarity in the example block diagram provided in FIG. 2, the connections between electrical energy source 218 and the electrical components of IMD 202 are not shown, as one skilled in the art would be familiar with such connections.

In certain embodiments, sense amplifier circuitry 222 can be configured to process physiologic signals that are used to trigger or modulate therapy delivery and are stored as physiologic signal data for later retrieval as described herein. Generally, sense amplifier circuitry 222 is coupled to electrical signal sense electrodes and/or physiologic sensors realized on or in wireless device 206, which will be situated at a site distanced from IMD 202. Alternatively (or additionally), sense electrodes may be realized on or in the housing of IMD 202. Alternatively (or additionally), sense electrodes may be connected to IMD 202 via feedthrough elements that traverse the housing of IMD 202.

In certain embodiments, transceiver antenna lead 204 is utilized to carry sensor signals that originate from wireless device 206, which includes suitably configured and situated physiologic sensors and/or sense electrodes. As such, in some cardiac applications, sense amplifier circuitry 222 is designed to receive electrical cardiac signals from transceiver antenna lead 204 and to process such signals to derive event signals reflecting the occurrence of specific cardiac electrical events, including atrial contractions (P-waves) and ventricular contractions (R-waves). These event-indicating signals are provided to processing architecture 210 for use in controlling the synchronous stimulating operations of IMD 202 in accordance with common practice in the art. In addition, these event indicating signals may be communicated, via uplink transmission, to one or more external communication devices via communication module 216.

Transceiver 212 is suitably configured to generate and receive RF signals that are transmitted and received by IMD 202 (via transceiver antenna lead 204) in connection with the RF transponder based techniques described herein. In this regard, transceiver 212 may be coupled to processing architecture 210, and transceiver 212 and/or processing architecture 210 may include a decoder element and an encoder element.

Communication module 216 may include or cooperate with one or more antennas (not shown). Communication module 216 may include or cooperate with any number of transmitters, any number of receivers, and/or any number of transceivers, depending upon the particular implementation.

For example, communication module 216 may cooperate with transceiver 212 to enable IMD 202 to perform telemetry communication with an external device, such as programmer 104 (see FIG. 1).

In example embodiments, therapy delivery circuitry 214 can be configured to control and regulate the delivery of electrical stimulation to the patient, e.g., cardioversion/defibrillation therapy pulses and/or cardiac pacing pulses delivered to the heart, or other electrical stimulation delivered to the brain, other organs, selected nerves, the spinal column, the cochlea, or muscle groups, including skeletal muscle wrapped about the heart. For example, IMD 202 may be suitably configured to control activation of wireless device 206 by transmitting an activation signal to wireless device using transceiver 212 and transceiver antenna lead 204. Alternatively, in certain embodiments, therapy delivery circuitry 214 can be configured as a drug pump delivering drugs into organs for therapeutic treatment or into the spinal column for pain relief. Alternatively, in certain embodiments, therapy delivery circuitry 214 can be configured to operate an implantable heart assist device or pump implanted in patients awaiting a heart transplant operation.

For the embodiment described herein, therapy delivery circuitry 214 is configured to generate appropriate activation signals for wireless device 206, where a given activation signal may include or convey commands, parameters, and/or instructions that influence the operation of wireless device 206. For cardiac applications, IMD 202 and wireless device 206 may be cooperatively configured to process the following commands, without limitation: a sense command; a pace command; a defibrillate command; and a status command. Briefly, the sense command instructs wireless device 206 to detect electromagnetic activity conducted by (or otherwise associated with) body tissue, fluid, mass, or the like, the pace command instructs wireless device 206 to generate at least one pacing pulse with its capacitor, the defibrillate command instructs wireless device 206 to generate at least one defibrillation pulse with its capacitor, and the status command instructs wireless device 206 to provide status information (e.g., charge status for a capacitor of wireless device 206) to IMD 202. Certain embodiments utilize 32-bit instructions to realize each command. These commands and the manner in which wireless device 206 responds to the commands will be described in more detail below.

Registers of memory 220 can be used for storing data compiled from sensed cardiac activity and/or relating to device operating history or sensed physiologic parameters. Generally, the data storage can be triggered manually by the patient, on a periodic basis, or by detection logic (e.g., within sense amplifier circuitry 222) upon satisfaction of certain programmed-in event detection criteria. If not manually triggered, in certain embodiments, the criteria for triggering data storage within IMD 202 is programmed via telemetry transmitted instructions and parameter values. If manually triggered, in some cases, IMD 202 includes a magnetic field sensitive switch (this may be a Hall effect sensor, or another received communications signal) that closes in response to a magnetic field, and the closure causes a magnetic switch circuit to issue a switch closed signal to processing architecture 210 which responds in a "magnet mode." For example, the patient may be provided with a magnet (e.g., incorporated into an external communication device) that can be applied over IMD 202 to close the switch and prompt processing architecture 210 to store physiologic episode data when the patient experiences certain symptoms and/or deliver a therapy to the patient. Following such triggering, in certain embodiments, event related data, e.g., the date and time, may be stored along with the stored periodically collected or patient initiated physiologic data. Typically, once stored, the data is ready for telemetry transmission on receipt of a retrieval or interrogation instruction.

Memory 220 may also be used to store data necessary to support the functionality of IMD system 200. For example, memory 220 may be configured to store one or more probe identifiers 228, where each probe identifier 228 identifies one wireless device (such as wireless device 206) in IMD system 200. In practice, each probe identifier 228 is unique throughout at least IMD system 200. Indeed, each probe identifier 228 may be unique on a global scale or on any suitable scale beyond that of IMD system 200. Moreover, memory 220 may be utilized to store information related to pre-programmed commands or instruction sets utilized by wireless device 206.

In certain embodiments, crystal oscillator circuit 208 generally employs clocked CMOS digital logic ICs having a clock signal provided by a crystal (e.g., piezoelectric) and a system clock coupled thereto as well as discrete components, e.g., inductors, capacitors, transformers, high voltage, protection diodes, and the like that are mounted with the ICs to one or more substrate or printed circuit board. Typically, each clock signal generated by the system clock is routed to all applicable clocked logic via a clock tree. In certain embodiments, the system clock provides one or more fixed frequency clock signals that are independent of the power supply voltage over an operating voltage range for system timing and control functions and in formatting telemetry signal transmissions. Again, the lines over which such clocking signals are provided to the various timed components of IMD 202 (e.g., processing architecture 210) are omitted from FIG. 2 for the sake of clarity.

Those of ordinary skill in the art will appreciate that IMD 202 may include numerous other components and subsystems, for example, activity sensors and associated circuitry. The presence or absence of such additional components in IMD 202, however, is not believed to be pertinent to the present invention, which relates to the implementation and operation of RF-based communication between IMD 202 and wireless device 206, and associated techniques and technologies.

In operation, IMD 202 uses transceiver antenna lead 204 to emit RF energy near the proximity of wireless device 206. This RF energy may serve to charge a capacitor of wireless device 206 using electromagnetic induction, to convey an activation signal having operating commands for wireless device 206, or the like. Notably, transceiver antenna lead 204 need not be routed through any valves in the heart for cardiac applications. Using transceiver antenna lead 204, IMD 202 can "interrogate" wireless device 206, which is configured as an RF transponder and which functions in a manner similar to an RFID tag when communicating with IMD 202.

Transceiver antenna lead 204 includes a connector end 230 configured for coupling to IMD 202, an antenna end 232, a flexible lead body 234 between connector end 230 and antenna end 232, and an RF lead antenna or coil 236 located proximate to antenna end 232. Two embodiments of transceiver antenna lead 204 will be described in more detail below with reference to FIG. 3, FIG. 4, and FIG. 6. In certain embodiments, transceiver antenna lead 204 may be considered to be a part of IMD 202 rather than a distinct component that couples to IMD 202.

Wireless device 206 (which may also be referred to here as a wireless semi-passive RF probe, an RF probe, an RF transponder, or a wireless therapy delivery transponder) is suitably configured for compatibility with IMD 202 and transceiver antenna lead 204. In particular, wireless device 206 is configured to respond to an "interrogation" by IMD 202 in a manner akin to an RFID tag. Wireless device 206 may include hardware, software, firmware, and circuitry for managing the operation and function of wireless device 206, with such features being contained within a hermetic enclosure of wireless device 206. Wireless device 206 may include, without limitation: an RF probe antenna or coil 238; a signal modulator 239; an electrode arrangement 240; a test module 241; a processing architecture 242; a sensor control module 243; a transceiver 244; an ECG module 245; a timer (sleep unit) 247; a capacitor 246; and a suitable amount of memory 248, which may include RAM and/or ROM. These elements may be coupled together using, for example, a bus 250 or any suitably configured interconnection arrangement. It should be appreciated that the configuration shown in FIG. 2 represents only one possible implementation of a wireless device suitable for use with IMD system 200.

For this example, wireless device 206 is configured for cardiac applications (e.g., to provide cardiac sensing, pacing, and/or defibrillation functions for the patient under the control of IMD 202). In particular, wireless device 206 may include the combined functionality of sensing, pacing, and defibrillating.

RF probe antenna 238 is suitably configured to receive and transmit RF energy in accordance with the techniques and technologies described herein. For example, RF probe antenna 238 is able to receive charge signals from RF lead antenna 236 such that wireless device 206 can charge capacitor 246 with energy derived from or conveyed by the charge signals. As another example, RF probe antenna 238 is able to receive activation signals from RF lead antenna 236, thus allowing IMD 202 to control the delivery of electrical therapy using wireless device 206. Moreover, RF probe antenna 238 is able to transmit signals for reception by RF lead antenna, e.g., status signals that convey information related to the operating status of wireless device 206.

Signal modulator 239 is a module that is configured to change and synchronize the frequency as determined by the particular mode of operation and/or the functionality of wireless device 206. Signal modulator 239 also functions to filter signals that could interfere with communications and charging of capacitor 246.

Electrode arrangement 240 is suitably configured to establish electrical contact with body tissue, fluid, muscle, etc. Electrode arrangement 240 may, for example, include two electrical conductors that are configured for attachment to (or placement within) designated tissue, fluid, or muscle of the patient. Electrode arrangement 240 may be configured to deliver electrical pulses to the patient via capacitor 246 and under the control of processing architecture 242. In this regard, electrode arrangement 240 is coupled to capacitor 246 in this embodiment. Thus, IMD system 200 need not utilize traditional endocardial leads routed through valves of the heart because wireless device 206 is configured to provide the functionality of such endocardial leads.

Additionally (or alternatively), electrode arrangement 240 may serve as sense electrodes for IMD system 200. In this regard, electrode arrangement 240 (possibly in conjunction with processing architecture 242) can be suitably configured to detect electromagnetic activity conducted by the patient's body tissue or fluid. In response to such detection, wireless device 206 can generate sensor signals that convey the electromagnetic activity detected by electrode arrangement 240, and transmit the sensor signals to RF lead antenna 236, using transceiver 244 and RF probe antenna 238.

Test module 241 represents a loop-back test unit that provides simulation and testing of the command architecture. Test module 241 provides result oriented responses based on sensing, without actual activation of the pacing or defibrillation circuits. For this example, test module 241 includes circuitry that can be used to debug and test the functionality of wireless device 206. A simple debug module with the appropriate probe I/O will help facilitate external calibration and probe diagnostics.

Processing architecture 242 may be generally configured and implemented as described above for processing architecture 210. Although specific connections between processing architecture 242 and other components of wireless device 206 are not shown in FIG. 2, it will be apparent to those of ordinary skill in the art that processing architecture 242 may be suitably configured to influence the operation of transceiver 244, capacitor 246, and memory 248. In other words, processing architecture 242 is designed to support the functionality of wireless device 206, which is described in more detail herein. For example, processing architecture 242 can be programmed to respond to sense commands, pace commands, defibrillate commands, status commands, and/or other commands that may be conveyed in activation signals originating from IMD 202. For ease of implementation, processing architecture 242 may utilize pre-defined instruction sets for carrying out commands for IMD system 200.

Sensor control module 243 controls the communications signals from the patient in the form of analog-to-digital data through a basic analog-to-digital converter circuit. Sensor control module 243 facilitates the collection of data from all sensors available to wireless device 206 or indirectly from paired (networked probes) "probe nodes." In practice, wireless device 206 may be available in styles that include pressure sensing and fluid sensing (vascular pressure and fluid buildup will be determined to provide data to be used to analyze and arrive at a therapy solution).

Transceiver 244 is suitably configured to generate and receive RF signals that are transmitted and received by RF probe antenna 238 in connection with the RF transponder based techniques described herein. In this regard, transceiver 244 may be coupled to processing architecture 242, and transceiver 244 and/or processing architecture 242 may include a decoder element and an encoder element.

ECG module 245 cooperates with sensor control module 243 to gather ECG data and to act on that data based on the received commands from IMD 202. For example, a correctly and identified signal has been received containing an instruction from IMD 202 as follows:

COMMAND (TX): SENSE, W?, V###, A###, D###

This command is transmitted by the IMD to the wireless device. In this command, W? is a specific wave, such as the "T" or the "P" wave (multi-waves may also be used), V### is the voltage to be utilized, A### is the current (amps) to be utilized, D### is the duration of the sensing, and T### is the target sensing value.

COMMAND (RX): SENSE, R####

This command is transmitted by the wireless device to the IMD. In this command, R#### represents status bits confirming the command requested and a decodable 32-bit return value that can be used to acquire probe operational stations, charge level, etc.

Timer 247 (also referred to here as a sleep unit) is responsible for managing internal timers on elements such as internal power measurements. Suitably configured logic will facilitate the request from the IMD to provide additional charge. Timer 247 may also be configured to manage signal strength and the logic needed to burst signal strength as needed. In addition, timer 247 may be configured to manage power saving logic to allow wireless device 206 to reduce power needs during moments where only sensing might be needed.

Capacitor 246 serves as a rechargeable power source for wireless device 206. In addition, capacitor 246 can serve as an electrical energy storage element that is discharged as needed to provide electrical therapy to the patient in the form of pacing pulses, defibrillation pulses, or the like. As mentioned above, wireless device 206 energizes capacitor 246 in response to charge signals received from IMD 202 via transceiver antenna lead 204 and RF probe antenna 238. Thus, wireless device 206 operates as a semi-passive component that need not rely on an active power source or a battery. Moreover, wireless device 206 is suitably configured to receive activation signals from IMD 202 via transceiver antenna lead 204 and RF probe antenna 238. In response to received activation signals, wireless device 206 controls delivery of electrical therapy from capacitor 246 to body tissue, fluid, or muscle of the patient, using electrode arrangement 240.

Considering the actual power needs associated with cardiac sensing, pacing, and defibrillation at individual probe sites, the capacitance of capacitor 246 would likely be on the order of one microfarad. With the advent of less power being needed due to probe placement and the reduction of resistance by providing power at point of need, a probe would likely not need to deliver more than about two joules of energy per defibrillation phase to provide adequate defibrillation to the cardiac patient. The need for larger amounts of power output can be accomplished through the rapid charge and discharge rate that is associated with RF technology.

Presently any capacitor that would be required in order to meet the one microfarad capacitance is size limited as it relates to the probe defibrillation expectations. However there are suitable capacitors available in both size and shape that can meet the sensing and pacing needs of the probe. As advancements increase with new power sources and the shape of the power sources through the use of advanced polymers (for flexibility in shape/size) and by using more exotic high energy materials, it is expected that the defibrillation needs can met using practical technologies.

Registers of memory 248 can be used for storing data compiled from sensed cardiac activity and/or relating to device operating history or sensed physiologic parameters. Generally, the data storage can be controlled by processing architecture 242, and such data storage may be influenced by commands received from IMD 202. Memory 248 may also be used to store data necessary to support the functionality of IMD system 200. For example, memory 248 may be configured to store a probe identifier 252 for wireless device 206, where probe identifier 252 is unique throughout at least IMD system 200. Indeed, probe identifier 252 may be unique on a global scale or on any suitable scale beyond that of IMD system 200. Moreover, memory 248 may be utilized to store information related to pre-programmed commands or instruction sets utilized by wireless device 206.

Wireless device 206 can use probe identifier 252 to determine whether a received activation signal is actually intended for it. For example, wireless device 206 may be suitably configured to disregard activation signals that do not convey probe identifier 252, and to only process activation signals that convey probe identifier 252 or data from which probe identifier 252 can be derived. Thus, even if wireless device 206 receives ambient energy having the correct modulation and frequency characteristics, it will not respond unless it is actually addressed by its unique probe identifier 252. Notably, even if a given wireless device 206 is not being addressed or interrogated, its capacitor may become charged in response to the ambient RF energy being used to interrogate other wireless devices within the IMD system. Such "maintenance" charging of the capacitors is desirable to ensure that the wireless devices will be ready to sense, pace, or defibrillate as needed.

In one preferred embodiment, each wireless device will receive data and a charge in the form of a unique ID (i.e., one that is specific to that wireless device), a command (e.g., a 32-bit instruction set), and command-specific parameters that the command will use to instruct the wireless device to perform a specific function. An example of a simple single line of data sent from an IMD to a wireless device may be as follows.

Command Samples

Transmit command (sent to the wireless device from the IMD):

1 . . . 128, ST, WT, D500

Receive command (sent from the wireless device to the IMD):

1 . . . 128, ST, R01FE

Commands Explored 1-128 bits: Unique 128 probe address;

Command: ST=Status, SE=Sense, PA=Pace, DE=Defib;

Parameters: Prefix Identifiable Sub-Parameters (e.g., WT);

Period: P#### (e.g., Period in ms);

Volts: V#### (e.g., Voltage);

Amps: A#### (e.g., Amperage);

Return code: R#### (Status bits confirming the command requested and a decodable 32-bit return value that can used to acquire operational status of the wireless device, charge level, etc.);

FLASH: Sample disable command which causes the probe to return to default settings (bleed capacitor power, clear all data bits, and wait for reactivation).

Although the leadless wireless probes are not intended to be GEN2 EPC compliant, in practice the probes would approximate a classification close to that of ECP Tag Class 4/5 (Read, Write, Power Source, Active Communications). The unique identification of the probes will be accomplished utilizing standards developed for the RFID industry. Each probe can use a unique 128 or 256 bit long number for individual probe identification. The proposed probe ID structure can be best stated as similar to that in use with ECP 96 class 3 structures (larger memory, read and write, sensors, semi-passive).

Certain embodiments may utilize a dense reader mode of operation. This is a mode of operation that prevents RF-based readers from interfering with one another when many are used in close proximity to one another. IMDs and wireless probes as described herein may employ an equivalent methodology. In this regard, IMDs hop between channels within a certain frequency spectrum and may be required to listen for a signal before using a channel. If an IME "hears" another device using that channel, it will proceed to another channel to avoid interfering with the device on that channel. This technique can be selected as a method for assuring that an individual's IMD only communicates with wireless devices for that individual.

Figure 3:
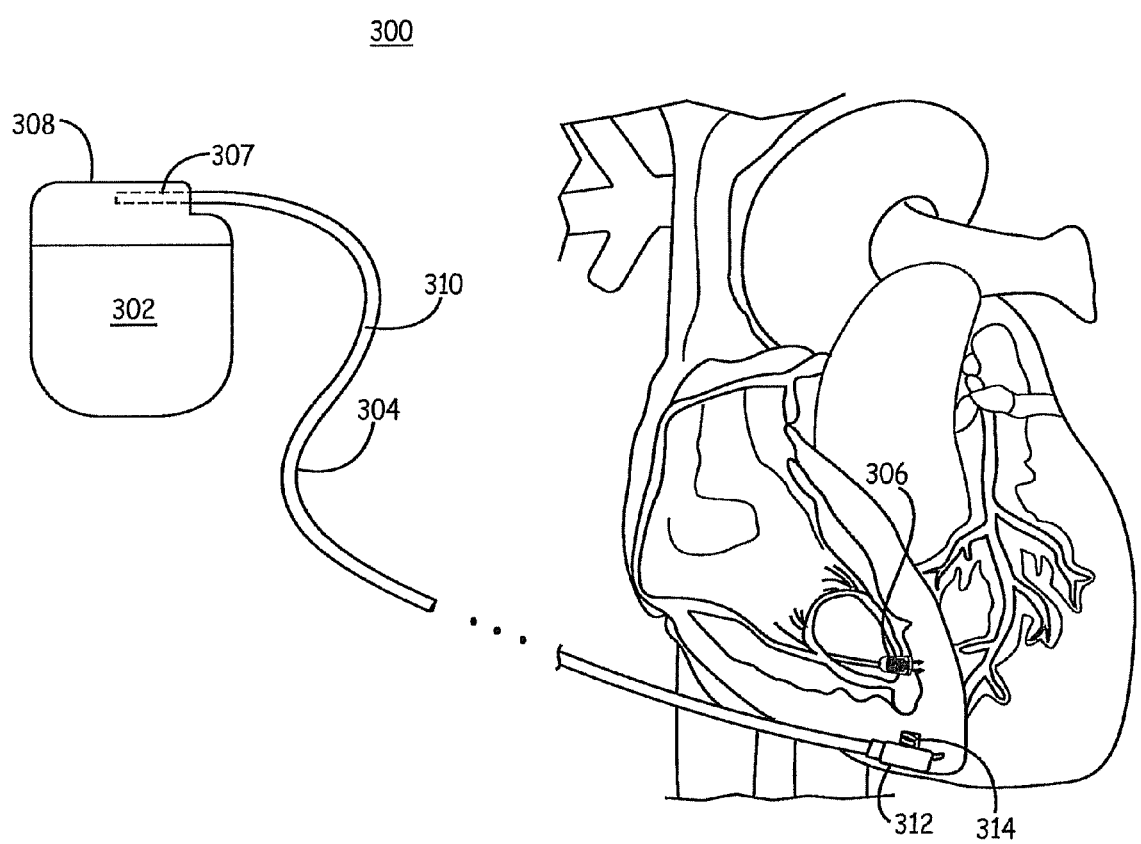
FIG. 3 is a diagram that illustrates one possible application for an embodiment of an RF transponder based IMD system.
Figure 4:
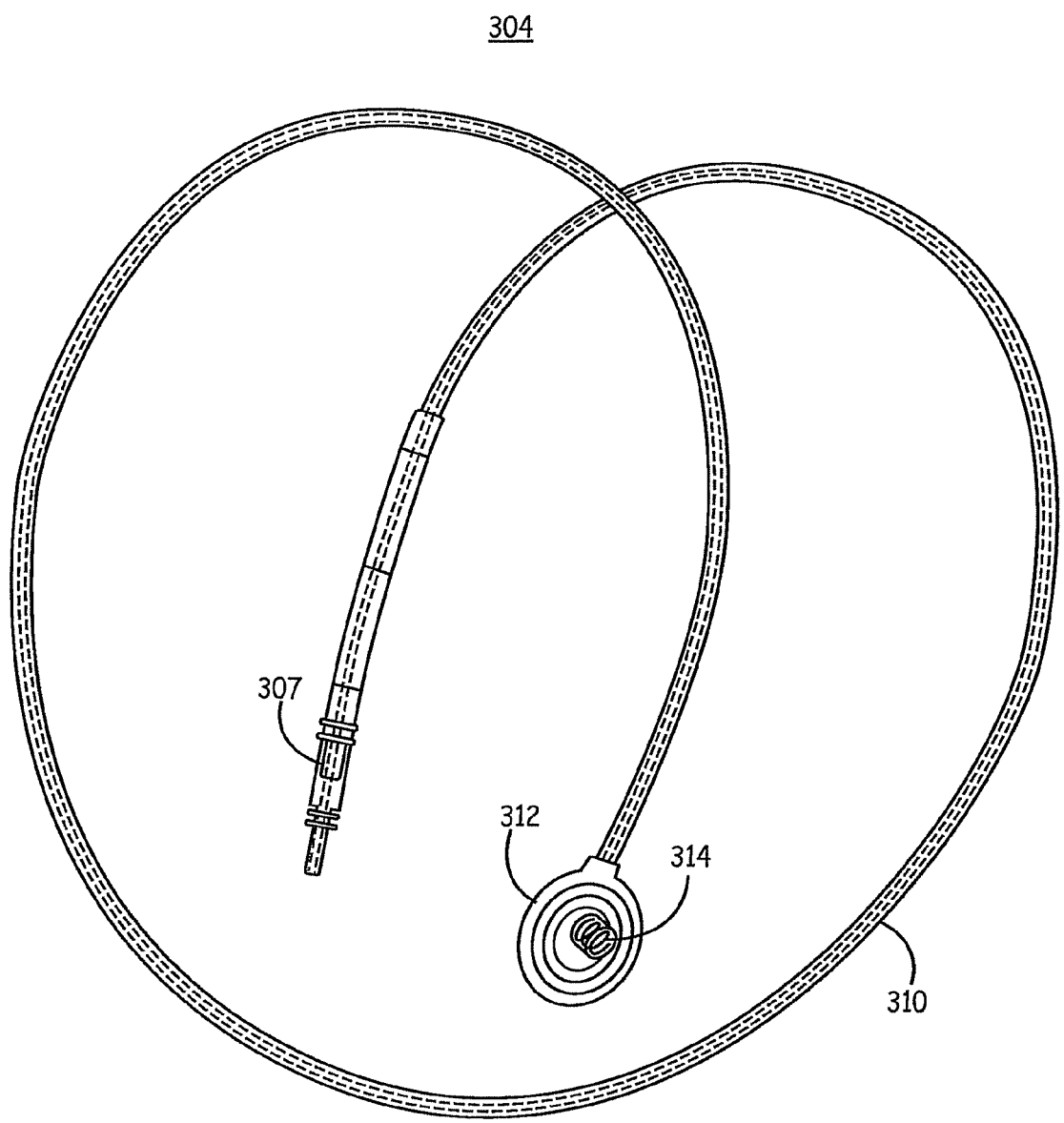
FIG. 4 is a perspective view of an embodiment of a transceiver antenna lead suitable for use in the IMD system shown in FIG. 3.
Figure 5:
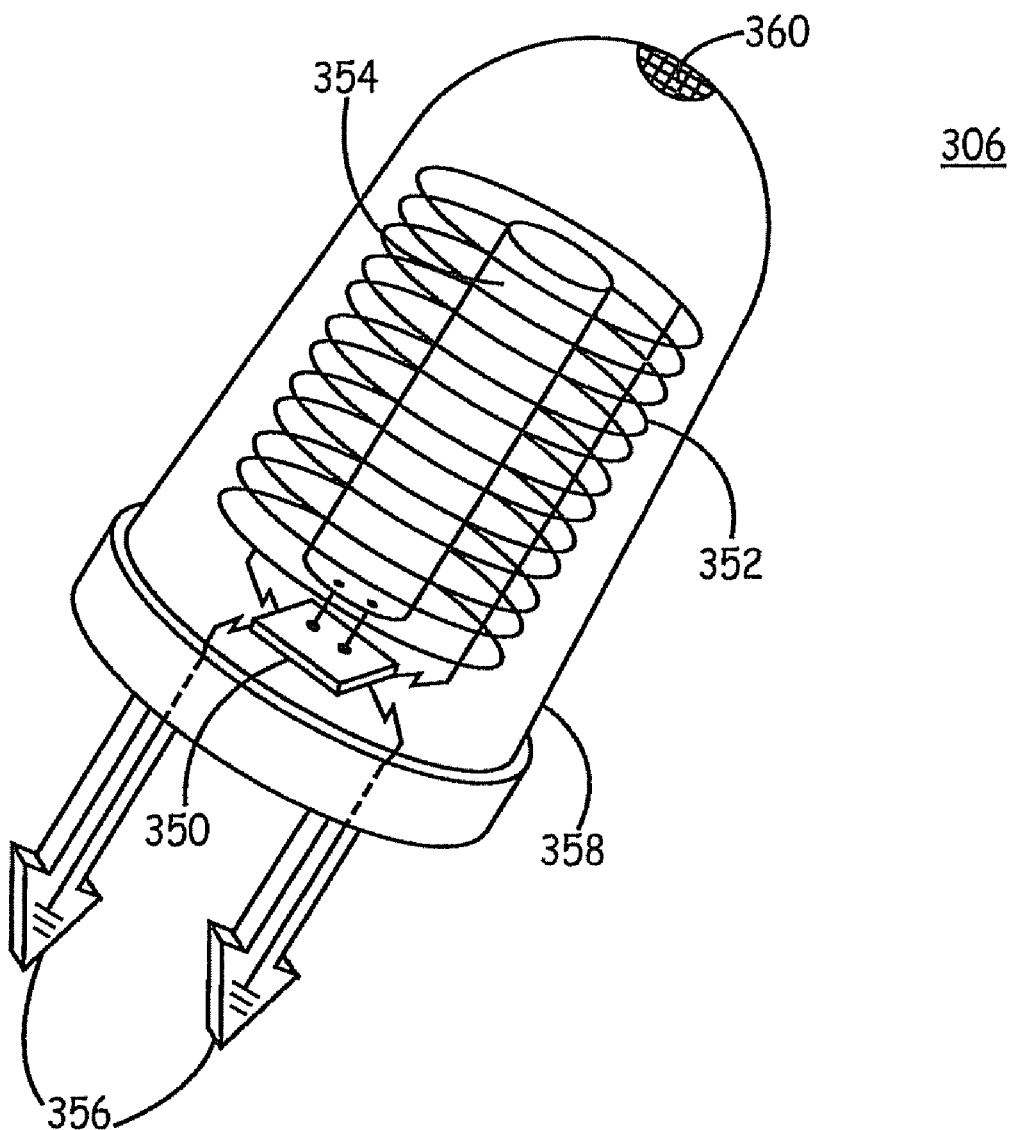
FIG. 5 is a schematic representation of an embodiment of a wireless semi-passive RF probe (transponder) suitable for use in the IMD system shown in FIG. 3.

FIG. 3 is a diagram that illustrates one possible application for an embodiment of an RF transponder based IMD system 300, FIG. 4 is a perspective view of an embodiment of a transceiver antenna lead 304 suitable for use in IMD system 300, and FIG. 5 is a schematic representation of an embodiment of a wireless semi-passive RF probe (transponder) 306 suitable for use in IMD system 300. IMD system 300 may implement the features and functionality of IMD system 200, and any common features, functions, or configurations will not be redundantly described here in the context of IMD system 300.

IMD system 300 generally includes an IMD 302, a transceiver antenna lead 304 coupled to IMD 302, and a wireless device 306 that communicates with IMD 302 via transceiver antenna lead 304. As mentioned above, one end 307 of transceiver antenna lead 304 is coupled to a connector block 308 of IMD 302. This end 307 may be sized and shaped in accordance with standard IMD lead configurations. Connector block 308 establishes the necessary electrical contacts from the conductors of transceiver antenna lead 304 to the internal circuitry of IMD 302. In this example, a flexible lead body 310 of transceiver antenna lead 304 terminates at an RF lead antenna 312. Flexible lead body 310 contains one or more electrical conductors (e.g., two wires) that feed RF lead antenna 312. RF lead antenna 312 can leverage known RF techniques and technologies, and RF lead antenna 312 may have any suitable design and topology that supports the desired application. For example, RF lead antenna 312 may be a directional antenna that emits RF energy in a focused direction, e.g., toward wireless device 306. In one embodiment, RF lead antenna 312 is configured to support 13.56 MHz signals that are formatted in accordance with an appropriate protocol. RF signals in this frequency range work well for IMD applications because the frequency is safe for body tissue and fluid, and because such RF signals propagate well through body tissue and fluid.

Transceiver antenna lead 304 may include one or more fixation members 314 that are configured to attach the antenna end of transceiver antenna lead 304, RF lead antenna 312, and/or flexible lead 310 to body tissue. In this regard, transceiver antenna lead 304 may employ any suitable attachment scheme, mechanism, technique, or methodology. For example, fixation member 314 may be realized as a prong or a corkscrew element that cooperates with body tissue or muscle to position RF lead antenna 312 as desired. Moreover, fixation member 314 itself may serve as RF lead antenna 312 (or an extension thereof).

The embodiment of wireless device 306 utilized in IMD system 300 resembles a small capsule-shaped LED (see FIG. 5). Wireless device 306 includes, without limitation: a processor 350; an RF probe antenna 352; a capacitor 354; an electrode arrangement of two electrodes 356; and a hermetically sealed enclosure 358. In addition to (or in lieu of) one of electrodes 356, wireless device 306 may employ an exposed electrode contact 360. For clarity, the internal electrical connection from electrode contact 360 to processor 350 is not depicted in FIG. 5. Electrode contact 360 may be desirable in certain applications that call for an increased separation between electrodes. As depicted in FIG. 5, wireless device 306 may be packaged in a compact form such that capacitor 354 is surrounded by RF probe antenna 352, which is implemented as a coil antenna in this example. Electrodes 356 may include pronged features or other features that facilitate attachment of wireless device 306 to body tissue or muscle.

In certain embodiments, when IMD system 300 is used for cardiac applications (e.g., to provide cardiac sensing, pacing, and/or defibrillation functions for the patient), one or more wireless device 306 is implanted in the patient's heart. In certain embodiments, with respect to such cardiac applications, the various electrodes in the wireless devices 306 can include atrial tip and ring electrode conductors, and ventricular tip and ring electrode conductors. Thus, stimulating pulses may be delivered by wireless devices 306 via the respective electrodes, under the control of IMD 302.

Figure 6:
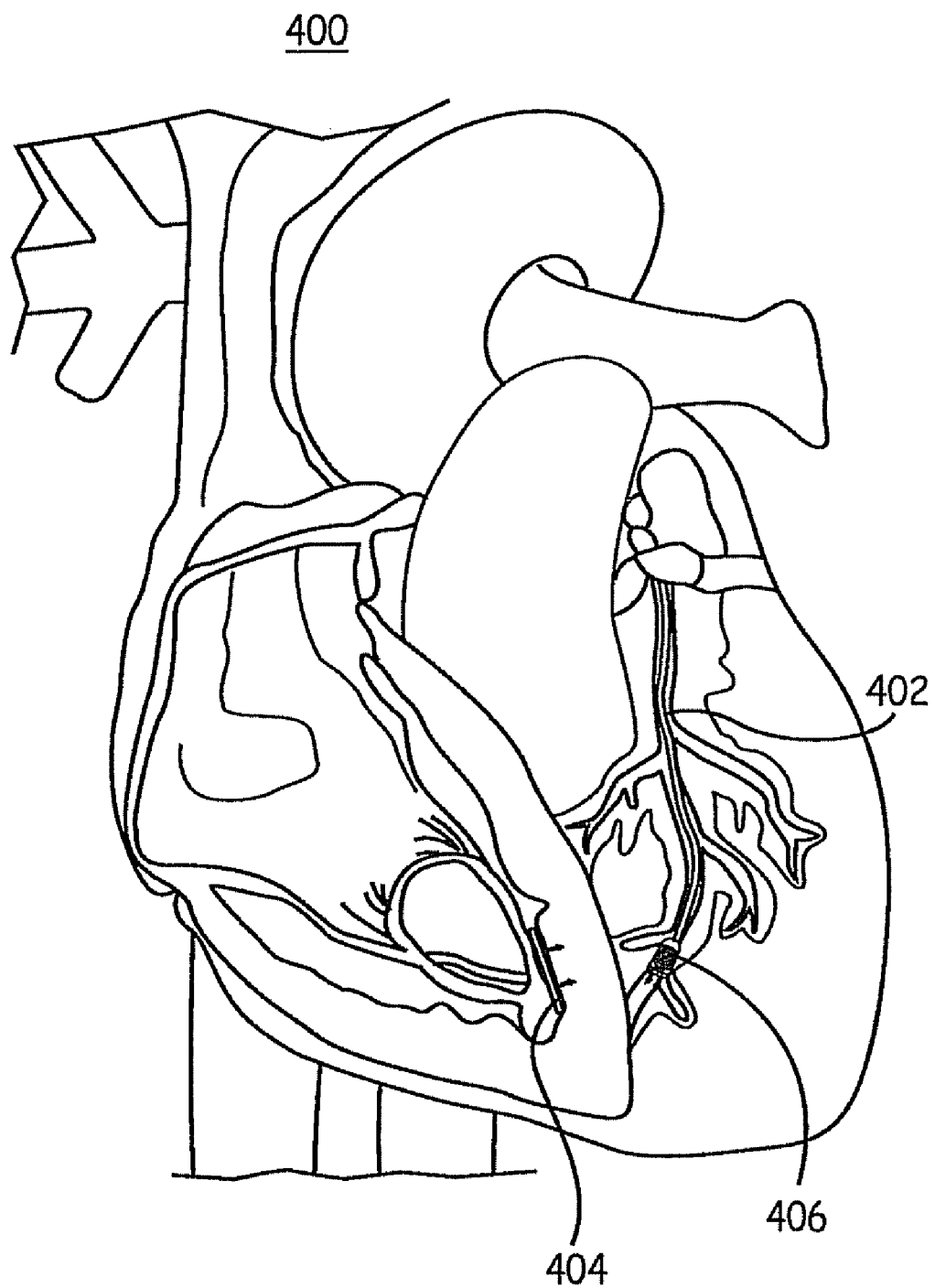
FIG. 6 is a diagram that illustrates another possible application for an embodiment of an RF transponder based IMD system.
Figure 7:
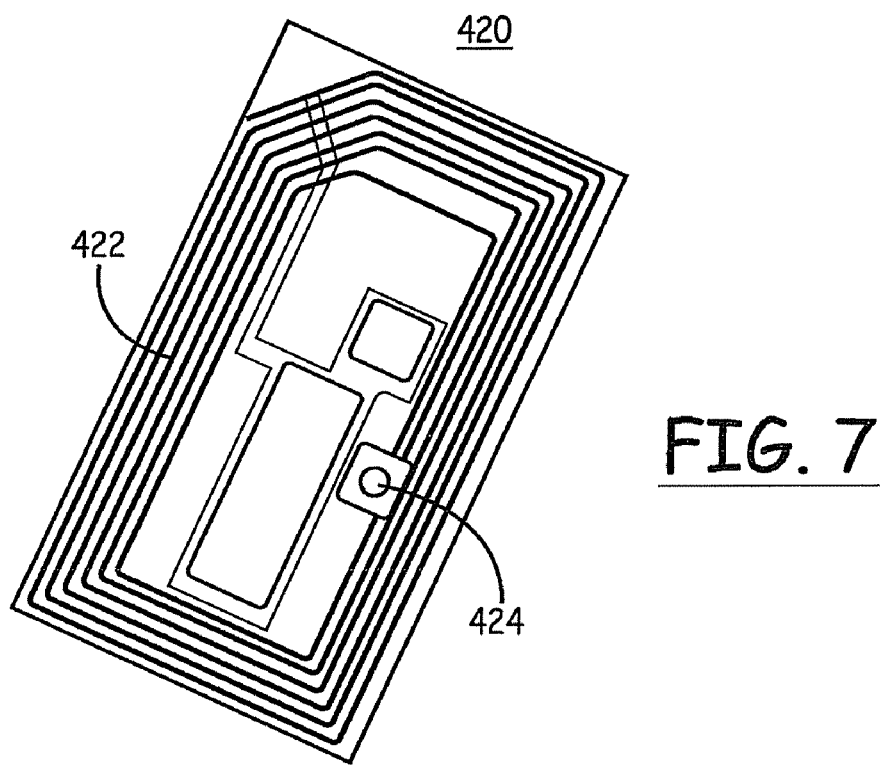
FIG. 7 is a plan view of a circuit board of an embodiment of a wireless semi-passive RF probe (transponder) suitable for use in the IMD system shown in FIG. 6.
Figure 8:
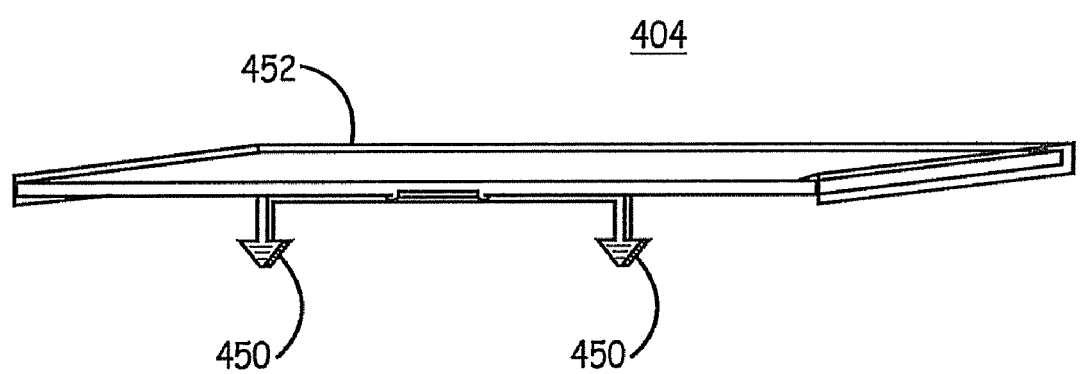
FIG. 8 is a schematic representation of an embodiment of a wireless semi-passive RF probe (transponder) suitable for use in the IMD system shown in FIG. 6.

FIG. 6 is a diagram that illustrates another possible application for an embodiment of an RF transponder based IMD system 400, FIG. 7 is a plan view of a circuit board 420 of an embodiment of a wireless semi-passive RF probe (transponder) suitable for use in IMD system 400, and FIG. 8 is a schematic representation of an embodiment of a wireless semi-passive RF probe (transponder) 404 suitable for use in IMD system 400. IMD system 400 may implement the features and functionality of IMD system 200, and any common features, functions, or configurations will not be redundantly described here in the context of IMD system 400. Moreover, features, functions, and operations of IMD system 400 that are common to IMD system 300 will not be redundantly described here.

IMD system 400 generally includes an IMD (not shown), a transceiver antenna lead 402 coupled to the IMD, and a wireless device 404 that communicates with the IMD via transceiver antenna lead 402. In this example, transceiver antenna lead 402 is sized, shaped, and configured for vascular insertion and routing. In this regard, FIG. 6 depicts transceiver antenna lead 402 in place within an anterior artery of the patient's heart. In such an embodiment, transceiver antenna lead 402 terminates at an RF lead antenna 406. In practice, RF lead antenna 406 may not be directional, i.e., it may emit RF energy in virtually all directions relative to the tip of RF lead antenna 406.

The nature of transceiver antenna lead 402 allows it to be routed such that RF lead antenna 406 is proximate wireless device 404 (such close proximity may not otherwise be attainable using an external RF lead antenna such as that shown in FIG. 3). In certain embodiments, transceiver antenna lead 402 includes a stent or a feature that functions as a stent. In such embodiments, RF lead antenna 406 itself, or a portion thereof, may form the stent. The stent is used as RF lead antenna 406, and the applicator is maintained as the transceiver lead while still allowing blood to flow through a mesh or membrane to reduce the effects of obstruction caused by transceiver antenna lead 402.

The embodiment of wireless device 404 utilized in IMD system 400 resembles a flat substrate, which may be contoured to accommodate the shape of the implant site and to reduce its overall encroachment on other body elements. Wireless device 404 generally includes the same components mentioned above for wireless device 306. In practice, wireless device 404 may include circuit board 420 formed on a suitable substrate. Referring to FIG. 7, circuit board 420 includes a printed coil antenna 422 around its perimeter, and a processor chip 424 coupled to antenna 422. Referring to FIG. 8, wireless device 404 may include electrodes 450 configured to establish electrical contact with body tissue or muscle, and a capacitor 452 realized in a flat form factor. Although not depicted in FIG. 8, capacitor 452 and electrodes 450 may be coupled to each other and to processor chip 424 to allow wireless device 404 to operate in the manner described herein. Circuit board 420 and capacitor 452 are preferably encapsulated in a hermetically sealed enclosure (not shown) such that electrodes 450 remain exposed. For example, these items may be encapsulated in epoxy resin or silicone.

Figure 9:
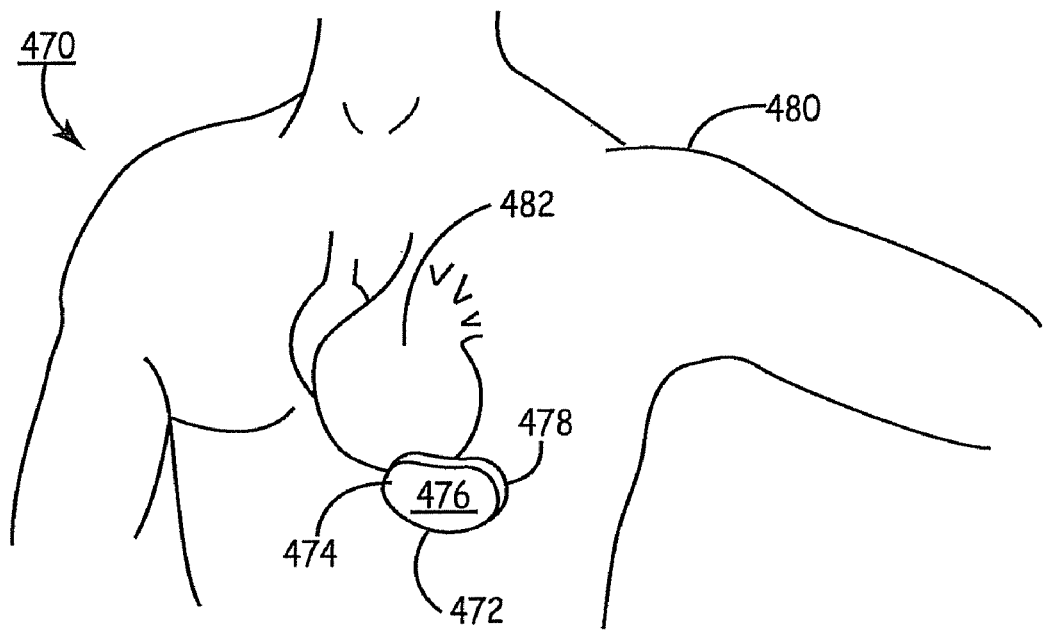
FIG. 9 is a schematic diagram of an exemplary subcutaneous device in which the present invention may be usefully practiced.
Figure 10:
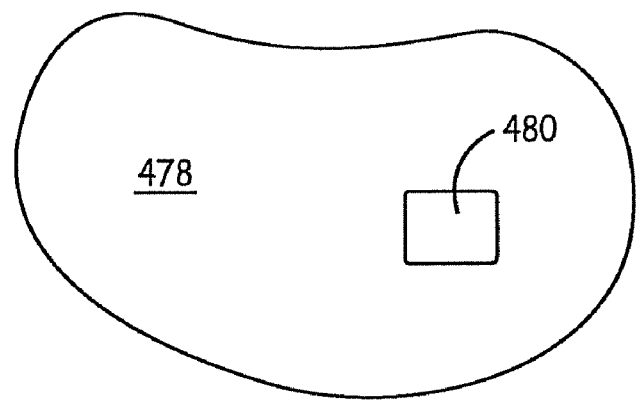
FIG. 10 is a plan view of a back side wall of a housing of the device of FIG. 9.

FIG. 9 is a schematic diagram of an exemplary subcutaneous device in which the present invention may be usefully practiced. FIG. 10 is a plan view of a back side wall of a housing of the device of FIG. 9. As illustrated in FIGS. 9 and 10, an IMD system 470 according to an embodiment of the present invention includes a subcutaneous device 472 having a housing 474 that includes a front side wall 476 and a back side wall 478, with an RF antenna member 480 positioned along the back side wall 478. Device 472 is subcutaneously implanted outside the ribcage of a patient 480, anterior to the cardiac notch of the patient's heart 482 to maximize the transmission of RF energy from RF antenna member 480 to the wireless device 306 (not shown in FIGS. 9 and 10) positioned within the heart 482 as described above.

Figure 11:
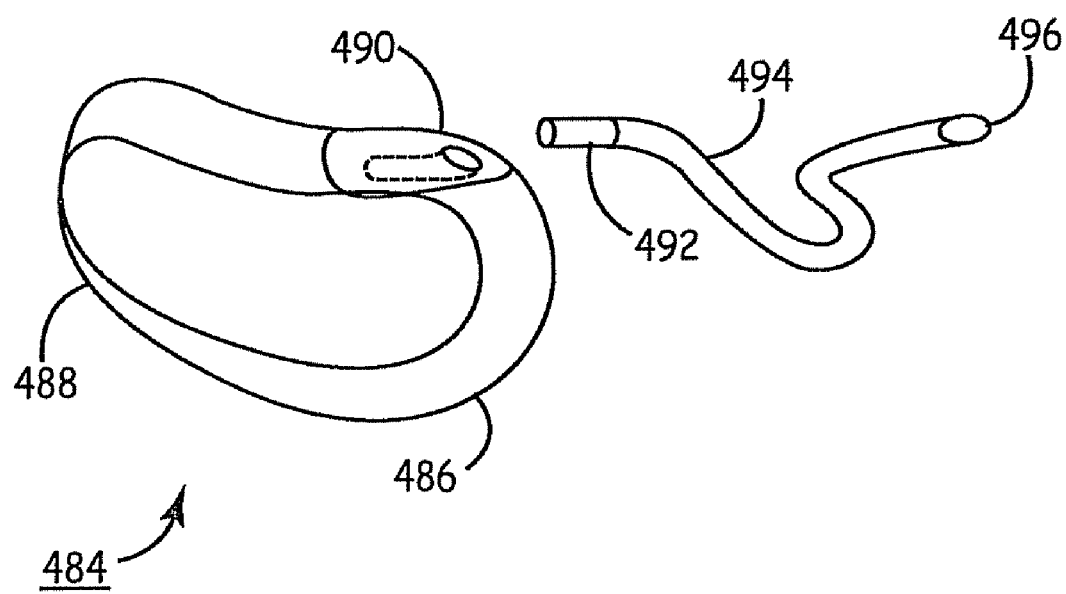
FIG. 11 is a schematic diagram of an exemplary subcutaneous device in which the present invention may be usefully practiced.

FIG. 11 is a schematic diagram of an exemplary subcutaneous device in which the present invention may be usefully practiced. As illustrated in FIG. 11, according to another embodiment of the present invention, an IMD system 484 includes a subcutaneous device 486 having a housing 488 and a connector block 490 position on the housing 488 for receiving a connector 492 on a proximal end of an elongated lead body 494 to electrically couple circuitry within housing 488 with an RF antenna member 496 positioned at the distal end of the lead body 494. In this way, device 486 may be subcutaneously positioned at any desired location, with lead body 494 being tunneled subcutaneously outward from the housing 488 to enable RF antenna member 496 to be positioned at a location to maximize the transmission of RF energy from RF antenna member 496 to the wireless device 306 (not shown in FIG. 11) positioned within the heart 482 as described above.

It is understood that while the subcutaneous device of FIGS. 9-11 is typically positioned through loose connective tissue between the skin and muscle layer of the patient, the term "subcutaneous device" is intended to include a device that can be positioned in the patient to be implanted using any non-intravenous location of the patient, such as below the muscle layer or within the thoracic cavity, for example.

Figure 12:
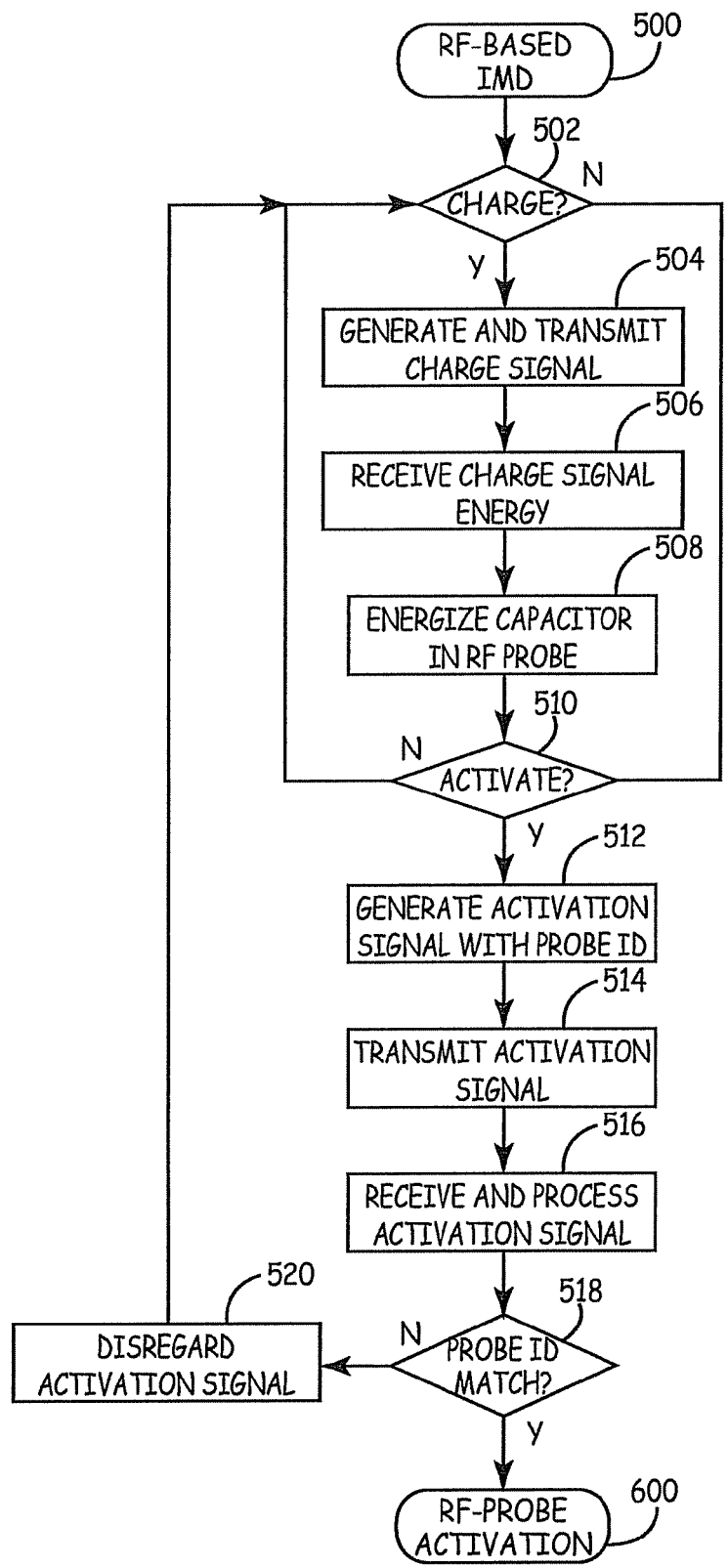
FIG. 12 is a flow chart that illustrates an embodiment of an RF-based IMD process.

Any of the IMD systems described herein can be utilized to provide RF transponder based communication between the IMD and the wireless device. In this regard, FIG. 12 is a flow chart that illustrates an embodiment of an RF-based IMD process 500. The various tasks performed in connection with process 500 may be performed by software, hardware, firmware, or any combination thereof. For illustrative purposes, the following description of process 500 may refer to elements mentioned above in connection with FIGS. 2-11. In practice, portions of process 500 may be performed by different elements of the described system, e.g., the IMD, the wireless device, or the transceiver antenna lead. It should be appreciated that process 500 may include any number of additional or alternative tasks, the tasks shown in FIG. 12 need not be performed in the illustrated order, and process 500 may be incorporated into a more comprehensive procedure or process having additional functionality not described in detail herein.

For this example, RF-based IMD process 500 controls the generation and transmission of charge signals and activation signals by the IMD. Depending upon the embodiment, however, process 500 need not support both functions. In certain embodiments, RF interrogation as described here may be performed up to 200 times per second. Consequently, process 500 can be performed in a multiplexed manner to support a plurality of wireless devices in a single patient without having to manage difficult or complex timing issues. The embodiment illustrated in FIG. 12 begins by checking whether a charge signal needs to be generated (query task 502). In practice, the decision to generate a charge signal can be made by the IMD alone or under the instruction, guidance, or influence of the wireless device, the patient (via a programmer, for example), a monitor device, or the like. Generally, a charge signal will be generated as needed to replenish the electrical energy stored in the capacitor of the wireless device. If a charge signal does not need to be generated, then process 500 may proceed to a query task 510 (described below).

If, however, query task 502 determines that a charge signal should be generated, then RF-based IMD process 500 generates and transmits a suitably configured charge signal (task 504). In practice, the IMD generates one or more charge signals for the wireless device, and then transmits each charge signal using its transceiver. Referring to FIG. 2, a charge signal will be transmitted or propagated through transceiver antenna lead 204 and from RF lead antenna 236. Due to the short distance between the RF lead antenna and the RF probe antenna, the wireless device will receive the energy corresponding to the charge signal or signals (task 506). The antennas are the conduits between the IMD and the transceiver of the wireless device, which controls data acquisition and communication. In practice, an electromagnetic charging field produced by the RF lead antenna can be constantly present when using multiple wireless devices. The interface between the IMD and the wireless devices utilizes field energy for powering and charging purposes and for triggering action at the wireless devices (as explained in more detail below). When the RF probe antenna of the wireless device is in the electromagnetic field emitted by the RF lead antenna, the wireless device detects the charge signal so that its capacitor can be energized.

Inductive coupling and propagation coupling may be used at one point or another. During the point where there is no charge available in the capacitor of the wireless device, the IMD will use propagated coupling for both communications and energy transfer. Once there is a suitable charge on the wireless device such that the wireless device functions as a semi-passive device, the IMD can switch to using inductive coupling for its link.

In response to the charge signal(s), the wireless device energizes its capacitor, resulting in more stored energy in the capacitor (task 508). The RF transponder operation of the IMD system facilitates this wireless energizing of the capacitor. In practice, the number of charge signals and the electromagnetic characteristics of each charge signal may be controlled by the IMD. The specific aspects of the signal frequency, strength, and duration will be determined based on responses derived during the probe activation phase, usage, and bio impedance (which could change over time). Probe initiated events can also determine the IMD signal response (propagated or inductive). Though it is expected that a frequency of 13.56 MHz as is standard for many RF-based tag designs will comprise the initial IMD signal, it is also expected that in order to meet the noise elimination needs of the system that the initial signal will vary based on determined need.

RF-based IMD process 500 may also check to determine whether an activation signal for the wireless device needs to be generated (query task 510). In practice, the decision to generate an activation signal can be made by the IMD alone or under the instruction, guidance, or influence of the wireless device, the patient (via a programmer, for example), a monitor device, or the like. Generally, an activation signal will be generated whenever the IMD system desires to take some action at the wireless device. If an activation signal does not need to be generated, then process 500 may exit or be reentered at an appropriate location, for example, at query task 502.

If query task 510 determines that an activation signal should be generated, then RF-based IMD process 500 generates (task 512) an appropriate activation signal that is formatted to control activation of the wireless device. For this example, the activation signal includes or conveys the probe identifier for the intended destination wireless device, and at least one command for the wireless device. A given command may include or be associated with, without limitation: an instruction set; operating parameters related to the commanded activity; or the like. Eventually, process 500 transmits the formatted activation signal (task 514) from the IMD to the wireless device. Referring to FIG. 2, the activation signal will be transmitted or propagated through transceiver antenna lead 204 and from RF lead antenna 236. Due to the short distance between the RF lead antenna and the RF probe antenna, the wireless device will receive the activation signal (task 516) and process the activation signal in an appropriate fashion. As mentioned above, the antennas are the conduits between the IMD and the wireless device, which is suitably configured to process received activation signals using electromagnetic coupling techniques. In practice, the interface between the IMD and the wireless devices utilizes field energy for conveying activation signals, which trigger certain actions at the wireless device (as explained in more detail below). When the RF probe antenna of the wireless device is in the electromagnetic field associated with an activation signal, the wireless device detects the activation signal and processes any command-specific data conveyed in the activation signal.

For this embodiment, the wireless device will analyze the activation signal to check whether the probe identifier conveyed in the activation signal matches the probe identifier for the wireless device (query task 518). If not, then the wireless device can disregard the received activation signal (task 520) and ignore any commands conveyed in the activation signal. Following task 520, RF-based IMD process 500 may exit or it may be re-entered at an appropriate location, for example, at query task 502. If the probe identifier matches, then process 500 may proceed to activate the wireless device in response to the activation signal. For this example, process 500 initiates an RF probe activation process 600 when query task 518 determines that the probe identifiers match. Thus, process 500 can be utilized to wirelessly activate the wireless device in response to activation signals that are transmitted by the IMD via the transceiver antenna lead.

Formatting of an activation signal will be based on the status command format as mentioned herein. Initial probe capacitance and configuration will be determined via an inductive coupling and the appropriate response from the IMD will be configured, for example: activate propagated coupling; charge probe using a signal strength determined by probe feedback and internal patient characteristics; set sampling rates and desired target events for probe monitoring. Probe usage will determine the frequency of recharge and communications between the probe and the IMD. IMD interrogation will be active at all times in the event the probe loses power or additional bio resistance reduces the probe's ability to bridge the gap between the IMD antenna and the probe antenna. The system is designed such that a full charge is not needed at the probe in order to facilitate therapy. The IMD will have adequate capability to control the charge and discharge of the probe(s) as is determined by the patient's therapy needs.

Figure 13:
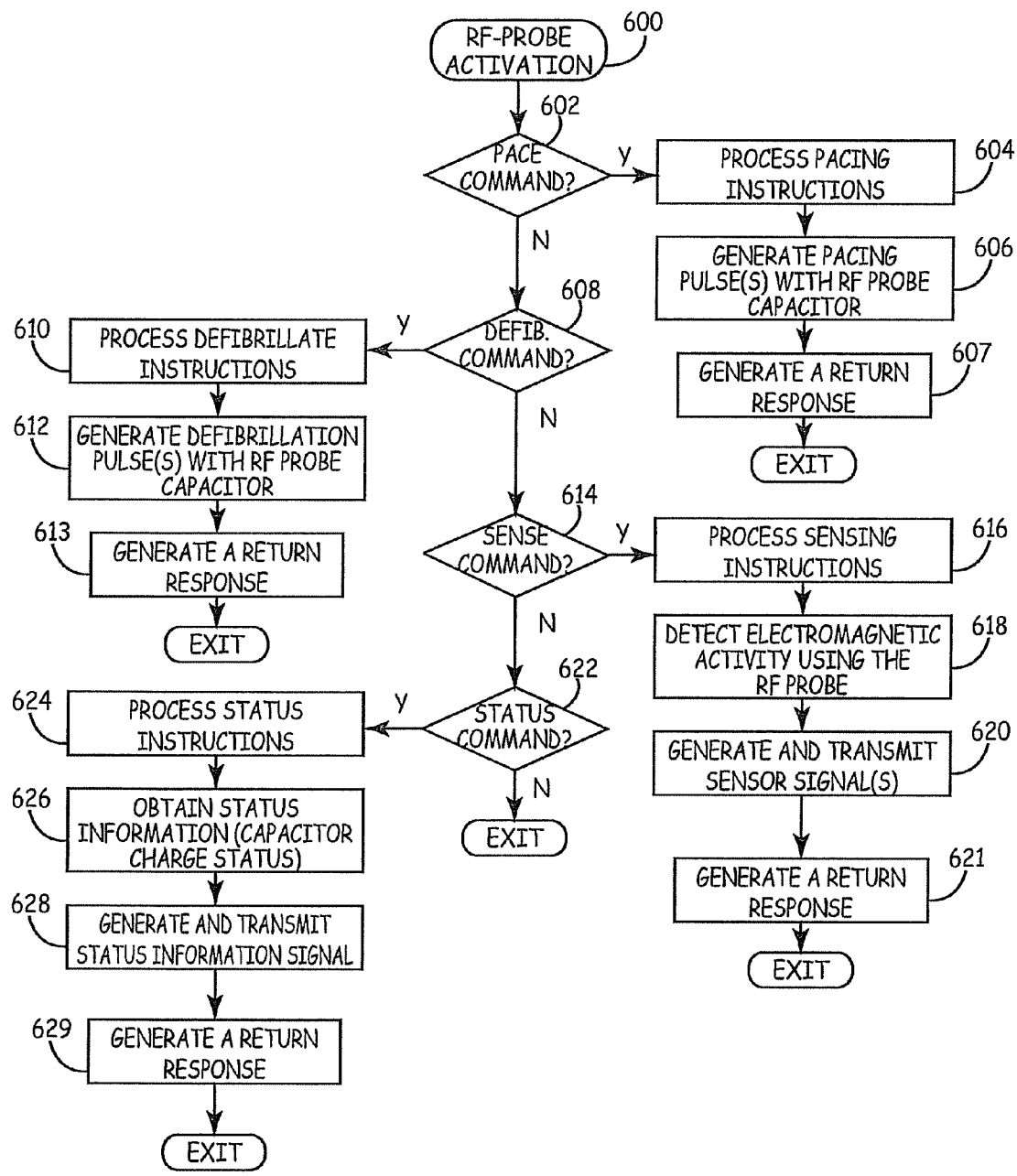
FIG. 13 is a flow chart that illustrates an embodiment of an RF probe activation process.

FIG. 13 is a flow chart that illustrates an embodiment of RF probe activation process 600, which may be prompted by RF-based IMD process 500. The various tasks performed in connection with process 600 may be performed by software, hardware, firmware, or any combination thereof. For illustrative purposes, the following description of process 600 may refer to elements mentioned above in connection with FIGS. 2-11. In practice, portions of process 600 may be performed by different elements of the described system, e.g., the IMD, the wireless device, or the transceiver antenna lead. It should be appreciated that process 600 may include any number of additional or alternative tasks, the tasks shown in FIG. 13 need not be performed in the illustrated order, and process 600 may be incorporated into a more comprehensive procedure or process having additional functionality not described in detail herein.

As mentioned above, an embodiment of an IMD system may be configured to support any number of commands or instruction sets. For simplicity and robustness, it may be desirable to limit the number of commands. For example, the embodiment described herein is configured to handle four primary commands (pace commands; defibrillate commands; sense commands; and status commands), and the commands are initiated by appropriately formatted activation signals generated by the IMD. Moreover, one activation signal may include or indicate any number of commands for the IMD system. For simplicity, the following example assumes that each activation signal is associated with only one command.

The illustrated embodiment of RF probe activation process 600 begins by checking whether the received activation signal conveys a pace command or data indicative of a pace command (query task 602). If so, then the wireless device may process pacing instructions (task 604) corresponding to the pace command. In practice, pacing instructions may be conveyed in the received activation signal in the form of specified parameters. Alternatively, pacing instructions may reside in the wireless device as pre-programmed instructions or parameters that are initiated by the pace command. Pacing instructions may include, without limitation, instructions related to: the magnitude of the pacing pulses; the duration of the pacing; the wave at which a pulse will be delivered (e.g., "P" wave or "T" wave); and the number of pulses that can be delivered over a specified period. Just as pacing can be directed to occur at specific times and for specific periods, so can cardiac sensing. For example, the wireless probe acts as a miniature ECG (aka EKG). The probe can determine timing between two waves (e.g., PR) or within multiple waves (e.g., QRS). In response to the pace command and/or the pacing instructions, the wireless device generates pacing pulse(s) with its capacitor (task 606). The pacing may continue as needed. Moreover, in response to the pace command, the wireless device may generate an appropriate return response (task 607) that confirms the command sent with its sublevel parameters, but also appends a suitably formatted return code (e.g., a 32-bit code) that conveys operational data of the wireless device. After processing the pace command and generating the return response, process 600 may exit to wait for the next activation signal, it may be re-entered at an appropriate location, e.g., at query task 608, or it may proceed in any desired manner.

RF probe activation process 600 may also check whether the received activation signal conveys a defibrillate command or data indicative of a defibrillate command (query task 608). If so, then the wireless device may process defibrillation instructions (task 610) corresponding to the defibrillate command. In practice, defibrillate instructions may be conveyed in the received activation signal in the form of specified parameters. Alternatively, defibrillate instructions may reside in the wireless device as pre-programmed instructions or parameters that are initiated by the defibrillate command. Defibrillate instructions may include, without limitation, instructions related to: the magnitude of the defibrillation pulses; the number of pulses to be applied; the frequency of pulses to be applied; or the like. In practice, the wireless device may utilize a relatively small capacitor that is able to store at least two joules of energy. In certain embodiments, the charge and discharge rate from the IMD to the wireless device may be about 20 times a second. In response to the defibrillate command and/or the defibrillate instructions, the wireless device generates defibrillation pulse(s) with its capacitor (task 612). The defibrillation procedure may continue as needed. Moreover, in response to the defibrillate command, the wireless device may generate an appropriate return response (task 613) that confirms the command sent with its sublevel parameters, but also appends a suitably formatted return code (e.g., a 32-bit code) that conveys operational data of the wireless device. After processing the defibrillate command and generating the return response, process 600 may exit to wait for the next activation signal, it may be re-entered at an appropriate location, e.g., at query task 614, or it may proceed in any desired manner.

RF probe activation process 600 may also check whether the received activation signal conveys a sense command or data indicative of a sense command (query task 614). If so, then the wireless device may process sensing instructions (task 616) corresponding to the sense command. In practice, sensing instructions may be conveyed in the received activation signal in the form of specified parameters. Alternatively, sensing instructions may reside in the wireless device as pre-programmed instructions or parameters that are initiated by the sense command. The sensing instructions may include, without limitation, instructions related to: which waveforms to detect; the duration of the sensing; or the like. The easiest way to indicate what the sensing function performs is to look at what a normal ECG (aka EKG) provides. The implanted probe will need to gather ECG data and, in an attempt to reduce the IMD requirement to analyze all data, the probe will process some of the data and filter down the amount of data that is transferred back to the IMD. In response to the sense command and/or the sensing instructions, the wireless device detects electromagnetic activity associated with body tissue, fluid, muscle, or the like (task 618). As described above, the electrode arrangement of the wireless device can be designed to accommodate such sensing. In response to the detection of electromagnetic characteristics, the wireless device generates and transmits one or more sensor signals that convey the detected electromagnetic activity (task 620). For this example, the IMD system employs the RF transponder techniques and technologies described above to communicate the sensor signals. In this regard, the sensor signals are transmitted by the transceiver of the wireless device, and the sensor signals are propagated from the RF probe antenna, to the RF lead antenna, through the transceiver antenna lead, and to the IMD, which processes the received sensor signals in an appropriate manner. The sensing procedure may continue as needed. Moreover, in response to the sense command, the wireless device may generate an appropriate return response (task 621) that confirms the command sent with its sublevel parameters, but also appends a suitably formatted return code (e.g., a 32-bit code) that conveys operational data of the wireless device. After processing the sense command, process 600 may exit to wait for the next activation signal, it may be re-entered at an appropriate location, e.g., at query task 622, or it may proceed in any desired manner. For example, if the wireless device is instructed to provide sense data regarding the amount of time between the P-R waves for 2000 ms and then pace on the "T" wave (based on preset or received parameters) with a specific voltage, amperage and duration, then process 600 may be controlled by a suitable script (recipe) that is executed based upon the receipt of a single command.

RF probe activation process 600 may also check whether the received activation signal conveys a status command or data indicative of a status command (query task 622). If so, then the wireless device may process status instructions (task 624) corresponding to the status command. In practice, status instructions may be conveyed in the received activation signal in the form of specified parameters. Alternatively, status instructions may reside in the wireless device as pre-programmed instructions or parameters that are initiated by the status command. Status instructions may include, without limitation, instructions related to: the specific data being requested; when to provide the status information; or the like.

Examples of the status command functions include, without limitation:

(1) Determine current energy reserves;

(2) Provide initial probe charge and configuration parameters;

(3) Provide loop-back testing of all available sensors (e.g., pressure, fluid, resistance, etc);

(4) Simulation testing of the probe processor for the purposes of guaranteeing a good startup and in the event there are changes to the IMD. The user will want to perform a full regression test on the probes to ensure that no adverse effects have developed.

(5) Some commands that can be activated by the status command will be held in memory by the probe. An example would be the "Flash" command. The flash command would instruct the probe to reset to factory default values. Using the flash command would ensure that any questionable commands, actions, or data would be destroyed in favor of a normal operational state.

In response to the status command and/or the status instructions, the wireless device obtains status information that indicates current operating conditions, parameters, and/or characteristics of the wireless device (task 626). In particular, the status information may include a charge status for the capacitor of the wireless device and/or a request to charge the capacitor. Thereafter, the wireless device can generate and transmit the status information (in the form of one or more status signals) to the IMD (task 628). For this example, the IMD system employs the RF transponder techniques and technologies described above to communicate the status signals. In this regard, status signals are transmitted by the transceiver of the wireless device, and status signals are propagated from the RF probe antenna, to the RF lead antenna, through the transceiver antenna lead, and to the IMD, which processes the received status signals in an appropriate manner. The status reporting procedure may continue as needed. Moreover, in response to the status command, the wireless device may generate an appropriate return response (task 629) that confirms the command sent with its sublevel parameters, but also appends a suitably formatted return code (e.g., a 32-bit code) that conveys operational data of the wireless device. After processing the status command and generating the return response, (or if query task 622 determines that the received activation signal does not convey a status command), process 600 may exit to wait for the next activation signal or it may proceed in any desired manner.

In summary, an RF-based sensing, pacing, and defibrillation IMD system as described herein employs RF technology to induce energy into a semi-passive wireless device, and then controls the use of energy stored at the wireless device for purposes of cardiac sensing, pacing, and/or defibrillation. The IMD system may leverage existing IMD platforms, which can be modified to support the RF-based techniques described herein while retaining their core functionality and feature sets. An IMD system as described herein can leverage normal cardiac procedures for placement of the IMD itself and any transceiver antenna leads. Notably, patient use of such an IMD system need not differ from methods that are presently used to control and monitor conventional IMD systems that utilize endocardial leads for sensing, pacing, and defibrillation.

While at least one example embodiment has been presented in the foregoing detailed description, it should be appreciated that a vast number of variations exist. It should also be appreciated that the example embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The invention claimed is:

1. An implantable medical system comprising:
an implantable medical device (IMD);
a transceiver antenna lead comprising a first end configured for coupling to the IMD and a radio frequency (RF) lead antenna proximate a second end thereof; and
a plurality of wireless RF probes to communicate with the IMD, wherein each wireless RF probe comprises:
an electrode arrangement to establish electrical contact with body tissue/fluid,
a capacitor coupled to the electrode arrangement,
an RF probe antenna to receive/transmit RF energy from/to the RF lead antenna,
probe memory to store processing instructions, and
a processing architecture to execute processing instructions stored in the probe memory to control delivery of therapy to body tissue/fluid or sensing of electromagnetic activity associated with body tissue/fluid.

2. The system of claim 1, wherein each wireless RF probe of the plurality of wireless probes is associated with a unique probe identifier, wherein the IMD is configured to control charging of the capacitor of each of the plurality of wireless RF probes by addressing each wireless RF probe using its unique probe identifier transmitted with a charge signal generated for transmission from the RF lead antenna to the wireless RF probe being addressed, and further wherein each of the wireless RF probes are configured to receive RF energy corresponding to the charge signal transmitted from the RF lead antenna useable to charge the capacitor of the wireless RF probe when being addressed by the IMD.

3. The system of claim 1, wherein each wireless RF probe of the plurality of wireless probes is associated with a unique probe identifier, wherein the IMD is configured to control activation of each of the plurality of wireless RF probes by addressing each wireless RF probe using its unique probe identifier transmitted with an activation signal from the RF lead antenna to the wireless RF probe being addressed, and further wherein each of the wireless RF probes are configured to receive the activation signal and process any command data conveyed in the activation signal.

4. The system of claim 3, wherein the processing architecture of the wireless RF probe is programmed to respond to at least one of a sense command that instructs the wireless RF probe to detect electromagnetic activity conducted by the body tissue/fluid, a pace command that instructs the wireless RF probe to generate at least one pacing pulse with the capacitor, a defibrillate command that instructs the wireless RF probe to generate at least one defibrillation pulse with the capacitor, and a status command that instructs the wireless RF probe to provide status information to the IMD.

5. The system of claim 1, wherein each wireless RF probe of the plurality of wireless probes is associated with a unique probe identifier, wherein the IMD is configured to interrogate each of the plurality of wireless RF probes via their unique probe identifier to provide one or more activation signals or charge signals thereto using RF energy, and further wherein each of the wireless RF probes is configured such that the capacitor thereof becomes charged in response to RF energy used to interrogate other wireless RF probes via their unique probe identifiers.

6. The system of claim 1, wherein each wireless RF probe of the plurality of wireless probes is associated with a unique probe identifier, wherein each of the wireless RF probes is configured to disregard activation signals that do not convey the unique probe identifier.

7. The system of claim 1, wherein the IMD and the plurality of wireless RF probes are configured to operate using a dense reader mode of operation.

8. The system of claim 1, wherein the processing architecture of each wireless RF probe is configured to execute processing instructions stored in memory to at least one of provide sense data or perform stimulation therapy using the electrode arrangement for a period of time without intervention by the IMD.

9. A method of operation in an implantable medical system comprising:
providing an implantable medical device (IMD), a transceiver antenna lead coupled to the IMD, and a plurality of wireless radio frequency (RF) probes, wherein each of the wireless RF probes includes an electrode arrangement to establish electrical contact with body tissue/fluid, a capacitor coupled to the electrode arrangement, an RF probe antenna, and a processing architecture;
generating, with the IMD, a charge signal for energizing at least one of the plurality of wireless RF probes;
transmitting the charge signal from the IMD, through the transceiver antenna lead, to charge the at least one wireless RF probe by energizing the capacitor thereof; and
controlling, with the processing architecture of the at least one wireless RF probe executing instructions stored in memory, the delivery of therapy to body tissue/fluid or the sensing of electromagnetic activity associated with body tissue/fluid using the electrode arrangement for a period of time without intervention by the IMD.

10. The method of claim 9, wherein each wireless RF probe of the plurality of wireless probes is associated with a unique probe identifier, and wherein generating a charge signal for energizing the at least one wireless RF probe comprises addressing the at least one wireless RF probe using its unique probe identifier transmitted with the charge signal.

11. The method of claim 9, wherein each wireless RF probe of the plurality of wireless probes is associated with a unique probe identifier, and further wherein the method comprises:
generating, with the IMD, an activation signal formatted to control activation of at least one of the plurality of wireless RF probes, wherein generating an activation signal comprises addressing the at least one wireless RF probe using its unique probe identifier transmitted with the activation signal; and
transmitting the activation signal from the IMD, through the transceiver antenna lead, to activate the at least one wireless RF probe in response to the transmitted activation signal to command the processing architecture to control delivery of therapy to body tissue/fluid or sensing of electromagnetic activity associated with body tissue/fluid.

12. The method of claim 11, wherein the processing architecture of the at least one wireless RF probe is programmed to respond to at least one of a sense command of the transmitted activation signal that instructs the wireless RF probe to detect electromagnetic activity conducted by the body tissue/fluid, a pace command of the transmitted activation signal that instructs the wireless RF probe to generate at least one pacing pulse with the capacitor, a defibrillate command of the transmitted activation signal that instructs the wireless RF probe to generate at least one defibrillation pulse with the capacitor, and a status command of the transmitted activation signal that instructs the wireless RF probe to provide status information to the IMD.

13. The method of claim 9, wherein each wireless RF probe of the plurality of wireless probes is associated with a unique probe identifier, wherein the method further comprises:
 addressing, with the IMD, one or more wireless RF probes of the plurality of wireless RF probes using their unique probe identifiers to provide one or more activation signals or charge signals thereto using RF energy; and
 replenishing energy to the capacitor of one or more wireless RF probes of the plurality of wireless RF probes not being addressed in response to the RF energy used to address the one or more wireless RF probes using their unique probe identifiers.

14. The method of claim 9, wherein the IMD and plurality of wireless RF probes are configured to operate using a dense reader mode of operation.

15. The method of claim 9, wherein generating, with the IMD, a charge signal for energizing the at least one of the wireless RF probes comprises:
 transmitting the charge signal from the IMD, through the transceiver antenna lead, to initially charge at least one wireless RF probe by energizing the capacitor thereof; and
 determining, after initial charging, whether a charge signal to wirelessly replenish the electrical energy in the capacitor should be generated and generating a charge signal based thereon.

16. The method of claim 15, wherein the method further comprises replenishing the electrical energy in the capacitor of the at least one wireless RF probe after initial charging with use of ambient RF energy available when the IMD interrogates one or more other wireless RF probes.

17. An implantable medical system comprising:
 an implantable medical device (IMD);
 a transceiver antenna lead comprising a first end configured for coupling to the IMD and a radio frequency (RF) lead antenna proximate a second end thereof; and
 a plurality of wireless RF probes to communicate with the IMD, wherein each wireless RF probe of the plurality of wireless probes is associated with a unique probe identifier, and further wherein each wireless RF probe comprises:
  an electrode arrangement to establish electrical contact with body tissue/fluid,
  a capacitor coupled to the electrode arrangement,
  an RF probe antenna to receive/transmit RF energy from/to the RF lead antenna, and
  a processing architecture,
 wherein the IMD is configured to interrogate each of the plurality of wireless RF probes via their unique probe identifier to provide at least charge signals thereto for charging the capacitor thereof using RF energy, and further wherein at least one of the wireless RF probes is configured such that the energy of the capacitor thereof is replenished in response to RF energy used to interrogate other wireless RF probes using their unique probe identifiers even though the at least one wireless RF probe is not being interrogated using its own unique probe identifier.

18. The system of claim 17, wherein the IMD is configured to control activation of each of the plurality of wireless RF probes by addressing each wireless RF probe using its unique probe identifier transmitted with an activation signal from the RF lead antenna to the wireless RF probe being addressed, and further wherein each of the wireless RF probes are configured to receive the activation signal and process any command data conveyed in the activation signal.

19. The system of claim 18, wherein the processing architecture of the wireless RF probe is programmed to respond to at least one of a sense command that instructs the wireless RF probe to detect electromagnetic activity conducted by the body tissue/fluid, a pace command that instructs the wireless RF probe to generate at least one pacing pulse with the capacitor, a defibrillate command that instructs the wireless RF probe to generate at least one defibrillation pulse with the capacitor, and a status command that instructs the wireless RF probe to provide status information to the IMD.

20. The system of claim 17, wherein the at least one wireless RF probe is configured such that the energy of the capacitor thereof is replenished in response to RF energy used to interrogate other wireless RF probes when transmitting an activation signal using the unique probe identifiers even though the at least one wireless RF probe is not being interrogated using its own unique probe identifier.

21. The system of claim 17, wherein the IMD and plurality of wireless RF probes are configured to operate using a dense reader mode of operation.

22. The system of claim 17, wherein the capacitor of at least one wireless RF probe comprises a capacitor having an energy storage capacity of at least two joules.

23. A method of operation in an implantable medical system comprising:
 providing a implantable medical device (IMD), a transceiver antenna lead coupled to the IMD, and a plurality of wireless radio frequency (RF) probes, wherein each of the wireless RF probes includes an electrode arrangement configured to establish electrical contact with body tissue/fluid, a capacitor coupled to the electrode arrangement, an RF probe antenna, and a processing architecture, and further wherein each wireless RF probe of the plurality of wireless probes is associated with a unique probe identifier;
 addressing, with the IMD, one or more of the wireless RF probes of the plurality of wireless RF probes using their unique probe identifiers to provide one or more charge signals thereto to initially charge the capacitors thereof;
 determining, after initial charging, whether a charge signal to wirelessly replenish the electrical energy in the capacitor of one or more of the wireless probes should be generated and generating one or more charge signals based thereon; and
 replenishing the energy in the capacitor of at least one wireless RF probe after initial charging with use of ambient RF energy available when the IMD addresses one or more other wireless RF probes using the unique probe identifiers to provide charge signals or activation signals comprising one or more commands to be executed by the addressed wireless RF probe.

24. The method of claim 23, wherein the IMD and plurality of wireless RF probes are configured to operate using a dense reader mode of operation.

25. The system of claim 23, wherein the capacitor of at least one wireless RF probe comprises a capacitor having an energy storage capacity of at least two joules.

* * * * *